United States Patent
Jensen

(10) Patent No.: US 6,725,076 B1
(45) Date of Patent: Apr. 20, 2004

(54) VECTOR VELOCITY ESTIMATION USING DIRECTIONAL BEAM FORMING AND CROSS CORRELATION

(75) Inventor: Jørgen Arendt Jensen, Lyngby (DK)

(73) Assignee: B-K Medical A/S, Gentofte (DK)

( * ) Notice: Subject to any disclaimer, the term of this patent is extended or adjusted under 35 U.S.C. 154(b) by 0 days.

(21) Appl. No.: 09/959,860

(22) PCT Filed: May 10, 2000

(86) PCT No.: PCT/DK00/00244

§ 371 (c)(1),
(2), (4) Date: Jan. 25, 2002

(87) PCT Pub. No.: WO00/68697

PCT Pub. Date: Nov. 16, 2000

(30) Foreign Application Priority Data

May 10, 1999 (DK) ........................ 1999 00634

(51) Int. Cl.[7] .............................. A61B 8/06
(52) U.S. Cl. ................ 600/407; 600/437; 367/89
(58) Field of Search ................ 600/453–456; 73/602, 861.25, 861.27, 861.31; 250/201.9; 340/936, 951, 953, 957; 356/121; 342/104–105, 107–108, 117; 367/89, 100, 125, 90

(56) References Cited

U.S. PATENT DOCUMENTS

| | | | | |
|---|---|---|---|---|
| 3,790,926 A | * | 2/1974 | Pekau | 343/8 |
| 4,244,026 A | * | 1/1981 | Dickey, Jr. | 364/565 |
| 4,693,319 A | * | 9/1987 | Amemiya | 73/861.25 |
| 4,744,367 A | * | 5/1988 | Kodama et al. | 73/861.25 |
| 4,905,209 A | * | 2/1990 | Huang | 367/125 |
| 4,922,255 A | * | 5/1990 | Berglind | 342/104 |
| 4,994,809 A | * | 2/1991 | Yung et al. | 367/89 |
| 5,000,184 A | * | 3/1991 | Bonnefous | 73/861.25 |
| 5,117,692 A | | 6/1992 | Moser | 73/626 |
| 5,378,888 A | * | 1/1995 | Stappaerts | 250/201.9 |
| 5,390,677 A | * | 2/1995 | Ferrera et al. | 73/861.25 |
| 5,409,010 A | | 4/1995 | Beach et al. | 128/661.09 |
| 5,586,063 A | * | 12/1996 | Hardin et al. | 364/561 |
| 6,148,224 A | * | 11/2000 | Jensen | 600/407 |
| 6,270,459 B1 | * | 8/2001 | Konofagu et al. | 600/449 |
| 6,464,637 B1 | * | 10/2002 | Criton et al. | 600/441 |

FOREIGN PATENT DOCUMENTS

| | | |
|---|---|---|
| EP | 0 616 231 A2 | 9/1994 |
| WO | WO 98/00719 | 1/1998 |

OTHER PUBLICATIONS

D.J. Phillips et al., "Should Results of Ultrasound Doppler Studies be Reported in Units of Frequency or Velocity?" *Ultrasound Med. Boil.*, 15:205–212, 1989.

M.D. Fox, "Multiple Crossed–Beam Ultrasound Doppler Velocimetry," *IEEE Trans. Son. Ultrason.*, SU–25:281–286, 1978.

G.E. Trahey et al., "Angle Independent Ultrasonic Detection of Blood Flow," *IEEE Trans. Biomed. Eng.*, BME–34:965–967, 1987.

V.L. Newhouse et al., "Ultrasound Doppler Probing of Flows Transverse with Respect to Beam Axis," *IEEE Trans. Biomed Eng.*, BME–34:779–788, 1987.

(List continued on next page.)

*Primary Examiner*—Francis J. Jaworski
(74) *Attorney, Agent, or Firm*—Finnegan, Henderson, Farabow, Garrett & Dunner, L.L.P.

(57) ABSTRACT

The two-dimensional velocity vector using a pulsed ultrasound field can be determined with the invention. The method uses a focused ultrasound field along the velocity direction for probing the moving medium under investigation. Several pulses are emitted and the focused received fields along the velocity direction are cross-correlated. The time shift between received signals is found from the peak in the cross-correlation function and the velocity is thereby determined.

20 Claims, 11 Drawing Sheets

OTHER PUBLICATIONS

O. Bonnefous., "Measurement of the Complete (3D) Velocity Vector of Blood Flows," *IEEE Ultrason. Symp.*, pp. 795–799, 1988.

.A. Jensen et al., "Calculation of Pressure Fields from Arbitrarily Shaped, Apodized, and Excited Ultrasound Transducers," *IEEE Trans. Ultrason. Ferroelec., Freq. Contr.*, 39:262–267, 1992.

Jørgen Arendt Jensen, *Estimation of Blood Velocities Using Ultrasound*, Cambridge University Press, p. 232, formula 8.16.

D.J. Phillips et al., "Should Results of Ultrasound Doppler Studies be Reported in Units of Frequency or Velocity?" *Ultrasound Med. Boil.*, 15:205–212, 1989.

M.D. Fox, "Multiple Crossed–Beam Ultrasound Doppler Velocimetry," *IEEE Trans. Son. Ultrason.*, SU–25:281–286, 1978.

G.E. Trahey et al., "Angle Independent Ultrasonic Detection of Blood Flow," *IEEE Trans. Biomed. Eng.*, BME–34:965–967, 1987.

V.L. Newhouse et al., "Ultrasound Doppler Probing of Flows Transverse with Respect to Beam Axis," *IEEE Trans. Biomed. Eng.*, BME–34:779–788, 1987.

O. Bonnefous., "Measurement of the Complete (3D) Velocity Vector of Blood Flows," *IEEE Ultrason. Symp.*, pp. 795–799, 1988.

A. Jensen et al., "Calculation of Pressure Field from Arbitrarily Shaped, Apodized, and Excited Ultrasound Transducers," *IEEE Trans. Ultrason. Ferroelec., Freq. Contr.*, 39:262–267, 1992.

\* cited by examiner

VECTOR VELOCITY ESTIMATION USING DIRECTIONAL BEAM FORMING AND CROSS CORRELATION

FIELD OF THE INVENTION

The invention relates to an apparatus and a method for determining the velocity vector of a remotely sensed object using either sound, in particular ultrasound, or electromagnetic radiation. The movement of the object is determined by emitting and receiving a pulsed field focused in the direction of the velocity vector. By using a number of pulse emissions, the inter pulse movement can be estimated and the velocity found from the estimated movement and the time between pulses. The invention is based on the principle of using a directionally focused field for making the received signal influenced by motion along the direction of the movement.

BACKGROUND OF THE INVENTION

Medical ultrasound is extensively used for studying flow dynamics in the human body by using color flow mapping. The technique displays a color image of the flow superimposed on the normal anatomic B-mode image. Traditionally, the velocity component along the ultrasound beam direction is measured, and a flow transverse to the beam is not displayed, since it is not measured or estimated. An example of this is shown in FIG. 1, where the flows in the carotid artery and the jugular vein are displayed. The image is acquired with a convex array transducer, and the angles between flow direction and the ultrasound beam change over the image. Notice the change of estimated flow direction around the dashed line in both vessels due to the change of angle between the flow and the ultrasound beam. This is one of the main limitations of current ultrasound flow systems, since most vessels are parallel to the skin surface, and therefore it is a problem to get a sufficiently small angle between the flow and the beam. Also the flow is often not parallel to the vessel surface, and it is therefore difficult, if not impossible, to estimate the correct angle and compensate for it [1]. In European patent application EP 616 231 [2] the velocity is found through a cross-sectional area using a 2D matrix transducer that can focus on the individual areas in the cross-section. The volume flow through the cross-section is then found, but still only the velocity in direction of the ultrasound beam is estimated. Several authors have attempted to remedy this artifact. Fox [3] suggested using two beams to find the transverse component. The system works well for large transducers and investigations close to the transducer, but the variance of the transverse component increases for situations with large depths and smaller transducers as used in cardiac scanning through the ribs. Trahey and co-workers [4] have suggested using speckle tracking in which a small search region in one image is correlated or compared to a subsequent image. This approach has problems in terms of frame rate, since images are compared, and the resolution of the velocity estimates can be low. Newhouse et al. [5] developed a method in which the total bandwidth of the received signal is affected by the transverse velocity. It is, however, often difficult to find this bandwidth due to the inherent noise in the signal.

Of special interest is the working by Bonnefous [6], which uses a number of parallel beams to find the transverse velocity. The approach does, however, not work for a velocity that is not orthogonal to the ultrasound beam direction.

In this invention a new technique using a focused signal in the direction of the velocity is used. The velocity is then found by acquiring two or more of these focused signals and cross correlating them to find the displacement between pulse emission, whereby the velocity can be determined.

PRIOR ART APPROACH

This section summarizes the article written in 1988 by Bonnefous [6], where a method for estimating the transverse velocity was suggested.

Transverse velocity estimation must perform a signal processing, where the effect of axial motion is negligible compared to the transverse one. The idea presented by Bonnefous requires a broad beam in emission (a plane ultrasound wave front), and a number of parallel identical beams, separated by a pitch w in the transverse direction, are generated in reception, see FIG. 2.

For a given depth z, the signal received $S_n(x,t)$ from the beam centered in x=0 is $$S_n(0,t) = \int p(x,t) D_n(x) dx \quad (1)$$

where p(x,t) is the response of a scatterer located at x in the ultrasound beam centered at x=0, and $D^n(x)$ is the scatterer distribution at the instant $nT_{prf}$, where $T_{prf}$ is the pulse repetition period. In the same way, the signal received from the beam centered at x=w is $$S_n(w,t) = \int p(x-w,t) D_n(x) dx \quad (2)$$

If only a transverse uniform motion of the scatterers in considered, the displacement between two consecutive pulses $nT_{prf}$ and $(n+1)T_{prf}$ will give the relation for the distribution of the scatterers $$D_{n+1}(x) = D_n(x - v_x T_{prf}) \quad (3)$$

where $v_x$ is the velocity of the scatterers. Combining equations (2) and (3) gives $$S_{n+1}(0,t) = \int p(x,t) D_{n+1}(x) dx = \int p(x,t) D_n(x - v_x T_{prf}) dx = \int p(x + v_x T_{prf}, t) D_n(x) dx S_{n+1}(0,t) = S_n(-v_x T_{prf}, t) \quad (4)$$

For a beam centered in x=w the relation between the consecutive signals is $$S_{n+1}(w,t) = S_n(w - v_x T_{prf}, t) \quad (5)$$

The signal received in x=w at the pulse time $(n+1)T_{prf}$ is, thus, the same as the signal received in a beam centered in $x = w - v_x T_{prf}$ at the pulse time $nT_{prf}$.

The correlation between the two signals p(x,t) and p(x−w,t) is an averaging of the received signals over the random scatterer distributions. The cross-correlation of the received signals from two adjacent signals is $$C_1(w) = \sum_n \int_{t_0}^{t_0 + \Delta t} S_n(0,t) S_{n+1}(w,t) dt \quad (6)$$

$$= \sum_n \int_{t_0}^{t_0 + \Delta t} S_n(0,t) S_n(w - v_x T_{prf}, t) dt$$

$$C_1(w) = C_0(w - v_x T_{prf}, t)$$

where $$C_0(w) = \sum \int_{t_0}^{t_0 + \Delta t} S_n(0,t) S_n(w,t) dt,$$

is the autocorrelation function averaged over a number of received lines, where the line number is denoted by n. The interval $(t_0, t_0+\Delta t)$ is the range gate selected for the received signals. Equation (6) show that the shift of $C_1$ compared with $C_0$ is the transverse displacement between the instants $nT_{prf}$ and $(n+1)T_{prf}$. Therefore, the maximum of $C_1(w)$ is $C_1(v_x T_{prf})=C_0(0)$.

For the general case, in which both axial and transverse motion takes place, the equation that relates the received signals from two successive pulses will be $$S_{n+1}(w, t) = S_n\left(w - v_x T_{prf}, t - \frac{2v_z T_{prf}}{c}\right) \quad (7)$$

Here $t_s = 2v_z T_{prf}/c$, is the time shift for the axial motion.

The cross-correlation and autocorrelation functions are generalized to two-dimensional functions and their expressions are $$C_1(w, u) = \sum_n \int_{t_0}^{t_0+\Delta t} S_n(0, t) S_{n+1}(w, t+u) dt \quad (8)$$

$$= \sum_n \int_{t_0}^{t_0+\Delta t} S_n(0, t) S_n\left(w - v_x T_{prf}, t - \frac{2v_z T_{prf}}{c} + u\right) dt \quad (9)$$

$$C_0(w, u) = \sum_n \int_{t_0}^{t_0+\Delta t} S_n(0, t) S_n(w, t+u) dt \quad (10)$$

The relation between the cross-correlation and the autocorrelation is $$C_1(w, u) = C_0\left(w - v_x T_{prf}, u - \frac{2v_z T_{prf}}{c}\right) \quad (11)$$

The two-dimensional determination of the velocity vector is performed by first finding the axial velocity and then the transverse component.

1. Axial velocity measurement: $C_1(0,u)$ is calculated and then, the time position of the correlation peak is determined as $$\text{Max}_u[C_1(0, u)] = C_1\left(0, \frac{2v_z T_{prf}}{c}\right) \quad (12)$$

2. Transverse velocity measurement: Fixing the value of the time coordinate to be $u=2v_z T_{prf}/c$ in $C_1(w, 2v_x T_{prf}/c)$, the peak for the transverse correlation is determined as $$\text{Max}_w\left[C_1\left(w, \frac{2v_z T_{prf}}{c}\right)\right] = C_1\left(v_x T_{prf}, \frac{2v_z T_{prf}}{c}\right) \quad (13)$$

This process can be generalized to measure the three-dimension velocity vector. New parallel beams along the y-axis should be used, and the cross-correlation function will be a three-dimensional function of the type $C_1(w,h,u)$. The problem with this approach is, however, that a spatially invariant velocity field is assumed, which is not the case in the human body.

SUMMARY OF THE INVENTION

This section describes the approach of the invention for finding the transverse component of the blood velocity. The invention presupposes that the direction of movement is known. In medical ultrasound a two-dimensional image including a blood vessel of interest is produced. The operator will then manually indicate the position and direction of the blood vessel to the system, or this information can be obtained automatically.

In a first embodiment of the invention, wave energy is emitted in a predetermined direction towards a moving object or a collection of moving objects, which will interact with the wave energy, whereby the wave energy will be scattered or reflected. Moving objects thus interacting with emitted wave energy are often referred to as "scatterers". Scattered or reflected wave energy will be received and processed to yield the desired estimate or measurement of velocity of the moving object or a collection of moving objects. The velocity of any scattering or reflecting object, whether emitting it self or not, can be measured.

The main idea of the first embodiment of the invention is the creation of a plurality of focal points, which together form a focused line or beam in the direction of the velocity vector that will track the motion of the scatterers. The generation of this focused beam requires a broad beam in emission and multiple foci along the line in reception. This can be achieved with a multi-element transducer. The focusing line is situated over the region of interest, where the motion of the scatterers occurs, see FIG. 3. The method of the invention presupposes that scatterers, whose motion is tracked, have the same velocity along the whole length of the line. When measuring a laminar parabolic flow or other spatially variant velocity fields, the focus line therefore has to be oriented in the direction of the flow lines.

The lateral beam is calculated during reception by delaying and adding responses from the individual elements of the array. The delays are found for each focus point by calculating the time it takes for the ultrasound wave to travel from each transducer elements to the focus point and back to the transducer. Lateral beams are in this way constructed for each of the emitted pulses.

The velocity is estimated from the cross-correlation of two consecutive lateral signals. Hereby the displacement of the signals corresponds to an estimate of the distance traveled by the scatterers in the lateral beam direction. Since the lateral beams are situated along the flow stream-lines, the complete velocity magnitude can be directly estimated.

In a second embodiment the velocity of a moving object or a collection of moving objects emitting wave energy while moving, is measured. No emission of wave energy is required, but rather the wave energy emitted by the moving object is received and processed to yield the desired estimate or measurement of velocity of the moving object or a collection of moving objects. The main idea of the second embodiment of the invention is the creation of a plurality of focal points, which together form a focused line or beam in the direction of the velocity vector that will track the motion of the emitting object or objects.

DETAILED DESCRIPTION OF THE INVENTION

Figure 1:
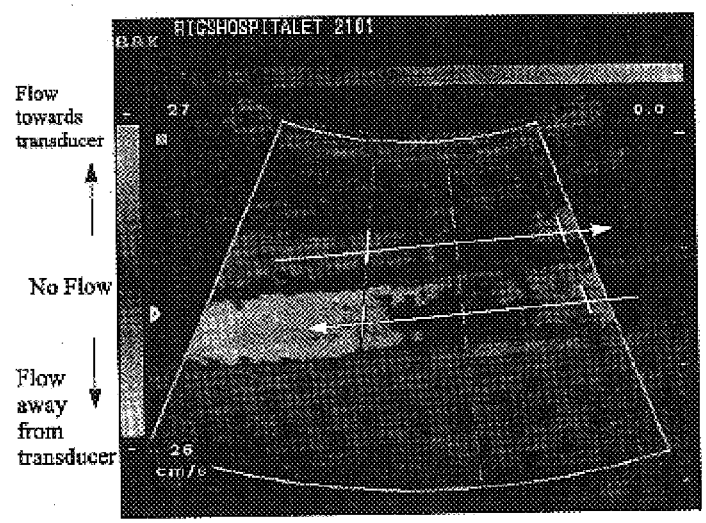
FIG. 1 is a flow image of the cartiod artery and the jugular vein scanned with a convex array transducer.
Figure 2:
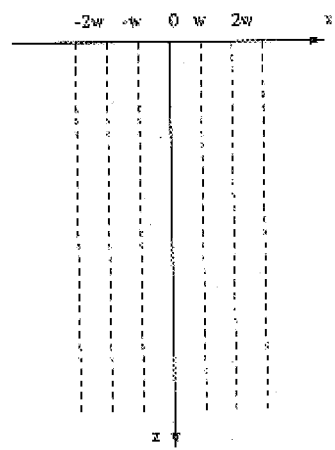
FIG. 2 illustrates parallel ultrasound beams in reception.

In FIG. 1 is shown an ultrasound flow image of the cartiod artery and the jugular vein of a human being scanned with a convex array transducer. Flow towards the transducer and flow away from the transducer will normally be shown in different colors such as red and blue, but here the colors are reproduced as different shades of gray. The dashed line is perpendicular to both blood vessels, and on both sides of the dashed line a black region indicates that no flow is registered in the direction of the dashed line. On both sides of the black no-flow region different shades of gray indicate the direction of flow as marked with arrows in FIG. 1.

Figure 1A:
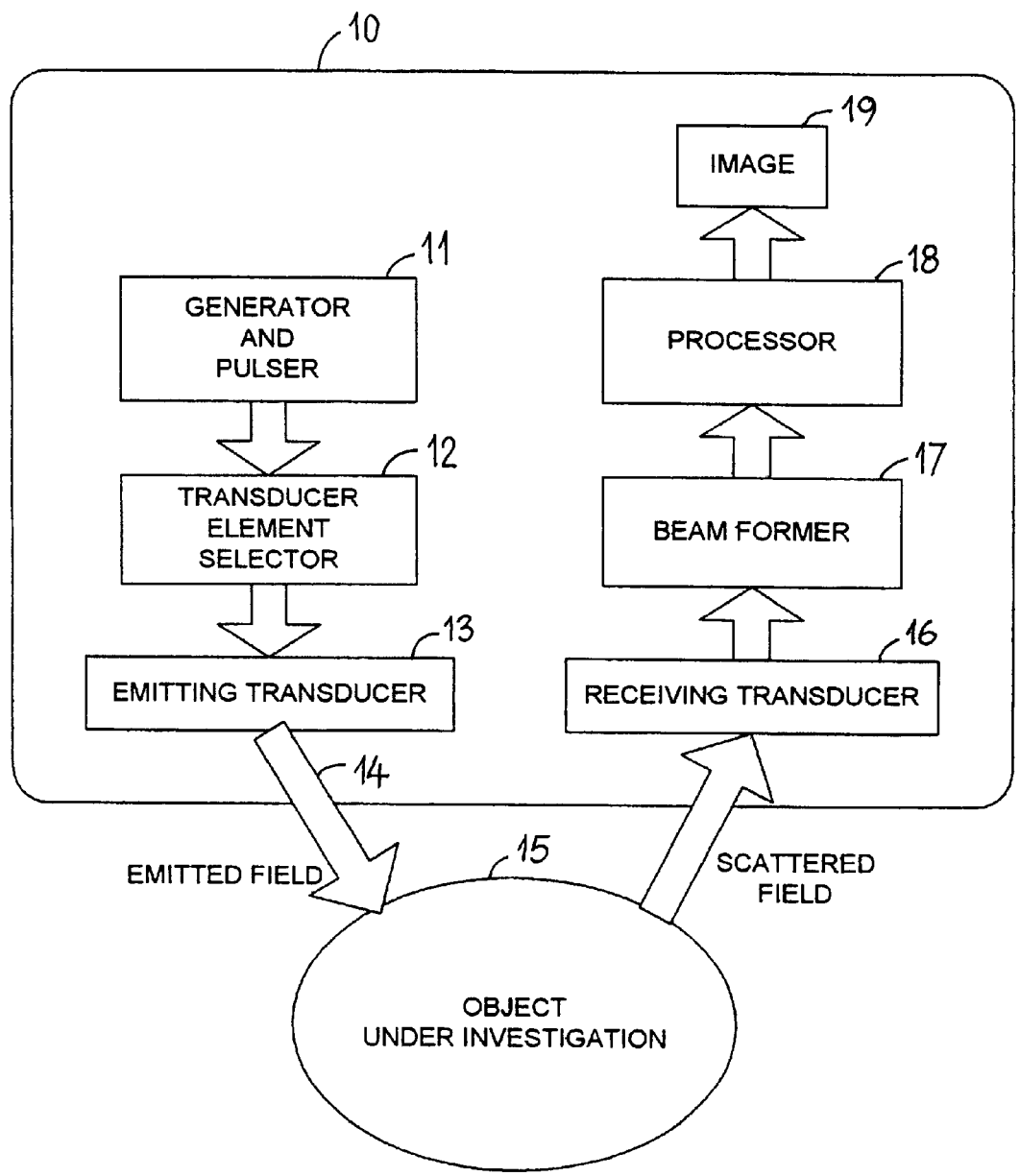
FIG. 1A is a schematic block diagram of an apparatus in accordance with the invention.

In FIG. 1A an apparatus 10 in accordance with the invention is shown schematically. A generator and pulser block 11 generates pulses of ultrasound frequency excitation signals. A transducer element selector block 12 receives the pulses of ultrasound frequency excitation signals from the generator and pulser block 11 and feeds the signals to selected ones of the transducer elements of an emitting transducer 13. The emitting transducer 13 is thereby caused to emit a beam 14 of ultrasound signals in a predetermined direction toward an object 15 under investigation. The object 15 under investigation interacts with the beam 14 of ultrasound signals and scatters the beam. A portion of the scattered ultrasound field 15 is received in a receiving transducer 16. In the receiving transducer 16 transducer elements output electric signals in dependence on the received ultrasound energy, and a beam former 17 receives the electric signals and performs a beam forming. The beam formed signals from the beam former 17 are received in a processor 18 that processes the beam formed signals into images 19.

Figure 3:
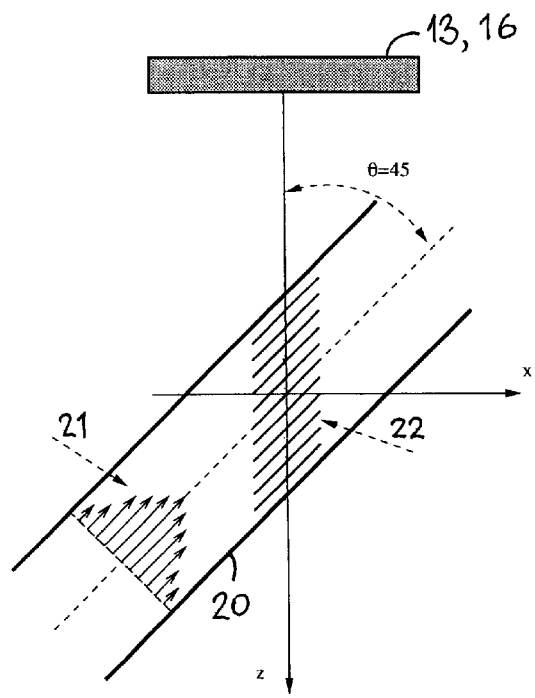
FIG. 3 illustrates focusing lines for obtaining lateral beams in the case of a parabolic velocity profile.

The object 15 under investigation can be the body of an animal or human being with blood vessel 20 of radius R in the body. In the blood vessel 20 the blood flow has a velocity profile 21, e.g. as indicated in FIG. 3. A plurality of focal points is combined to define a focusing line 22 or focusing beam in then predetermined direction of flow as in FIG. 4. The focusing line 22 can be placed anywhere in the blood vessel 20, and a plurality of lateral beams 22 can be formed as in FIG. 3.

Measurement Principle of the Invention

Figure 4:
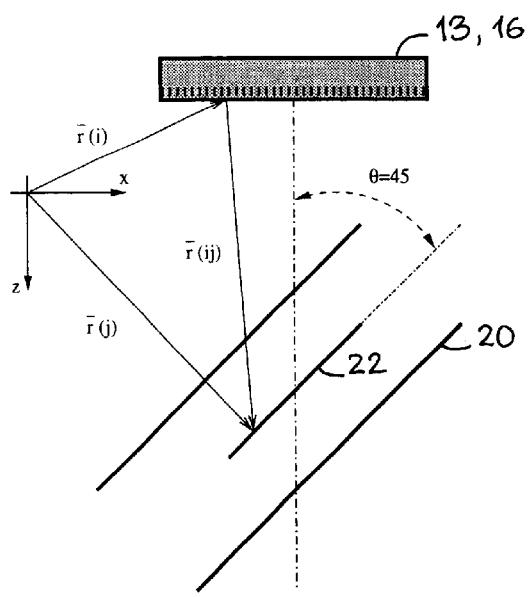
FIG. 4 shows a coordinate system for the lateral beam measurement principle.

This section derives a mathematical model of the tilted beam approach. The measurement situation is depicted in FIG. 4. The figure shows a multi-element transducer with N elements. The vector from the origin of reference to the physical center of element i is $\vec{r}_i$. The vector indicating the position of the focus points in the line is $\vec{r}_j$ and is given by $$\vec{r}_i=(x_i,y_i,z_i), i=1\ldots N \quad \vec{r}_j=(x_j,y_j,x_j), j=1\ldots M \quad \vec{r}_{ij}=\vec{r}_j-\vec{r}_i=(x_j-x_i,y_j-y_i,z_j-z_i), \tag{14}$$

where $\vec{r}_{ij}$ is the vector from element i to the focus point j, and M is the number of focus points along the line. The time it takes for the ultrasound pulse to get from the element i to the focus point j and back to the element i is $$t_{ij}2/c|\vec{r}_{ij}|=2/c\sqrt{(x_j-x_i)^2+(y_j-y_i)^2+(z_j-z_i)^2} \tag{15}$$

The received backscattered signal in element i that corresponds to the ultrasound pulse emitted in $nT_{prf}$, can be written as $r_n(\vec{r}_i,t)$, where t indicates the time since pulse emission.

Assuming linearity the value of the field in a focus point j, is calculated by adding the responses found in each element i for the appropriated delay time $t_{ij}$ $$s_n(\vec{r}_j) = \sum_{i=1}^{N} r_n(\vec{r}_i, t_{ij}) \tag{16}$$

For the next ultrasound pulse $(n+1)T_{prf}$, the value of the field in the same point will be $$s_{n+1}(\vec{r}_j) = \sum_{i=1}^{N} r_{n+1}(\vec{r}_i, t_{ij}) \tag{17}$$

$$= \sum_{i=1}^{N} r_n\left(\vec{r}_i, t_{ij} - 2\frac{v_{i,axis}}{T_{prf}}\right),$$

where $v_{i,axis}$ represents the component of the velocity of a scatterer placed in $\vec{r}_j$, projected on the $\vec{r}_{ij}$ direction. The expression above uses the relation between two consecutive backscattered signals. The relation $t_{ij}-2v_{i,axis}/T_{prf}$ will correspond to a delay value $t_{ik}$, where k is another point on the focusing line. If $\vec{d}_l$ is a unitary vector in the direction of the lateral beam, and $l_s$ is the distance between the points j and k, then $\vec{r}_j=\vec{r}_k+l_s\vec{d}_l$ and the following relation is found $$s_{n+1}(\vec{r}_j) = \sum_{i=1}^{N} r_n\left(\vec{r}_i, t_{ij} - 2\frac{v_{i,axis}}{T_{prf}}\right) \quad (18)$$

$$= \sum_{i=1}^{N} r_n(\vec{r}_i, t_{ik})$$

$$s_{n+1}(\vec{r}_j) = s_n(\vec{r}_k) = s_n(\vec{r}_j - l_s\vec{d}_l)$$

The beam processing is performed on digital signals and the sampled version of the beam formed signal is denoted $R_n[l]$. The signal calculated for the pulse at time $(n+1)T_{prf}$ is a shifted version of the lateral signal for the pulse at time $nT_{prf}$. The shift in position can be calculated from the cross-correlation of two consecutive signals $S_1[l]$ and $S_2[l]$:

$$R_{12} = \frac{1}{M}\sum_{l=0}^{M-1} S_1[l]S_2[l+n] \quad (19)$$

$$= \frac{1}{M}\sum_{l=0}^{M-1} S_1[l]S_1[l+n-l_s]$$

$$= R_{11}(k - l_s)$$

The shift in position is then determined by the index of the peak of the cross-correlation function $$\max_k[R_{12}(k)] = \max_k[R_{11}(k - l_s)] \Rightarrow k = \hat{l}_s \quad (20)$$

The cross-correlation can be improved by averaging over several estimates of $R_{12}$, since the velocity of the scatterers can be considered constant for several pulses. The estimated mean velocity between two consecutive pulses is:

$$\hat{v} = \frac{\hat{l}_s dl}{T_{prf}} \quad (21)$$

where dl is the sampling interval along the lateral beam direction.

Functionality of the Invention

The invention was simulated using the simulating program Field II [7]. The lateral beam is directly calculated with a focusing strategy that can be achieved with a regular array transducer. The method was first tested for a blunt profile of the scatterers and then for a parabolic profile.

Estimation of the Velocity for a Blunt Profile

In the beginning, the lateral beam was intended as an attempt to estimate the transverse velocity component ($\hat{v}_x$). Since $\hat{v}_z$ could be obtained from the time-shift estimation method, the velocity in the x–z plane will be estimated as $\vec{v}_{est}=(\hat{v}_x,\hat{v}_z)$.

The estimation of $v_x$ can be obtained in the case of a blunt profile using a focusing line perpendicular to the z-axis. Two lateral signals are generated for each ultrasound pulse. The second one has been compensated for the axial movement that took place in the pulse interval time. The cross-correlation of the first signal obtained from pulse i with the compensated signal from pulse i+1 reveals the transverse motion of the scatterers between the two pulses.

The calculation of the lateral beam and the estimation of the velocity are explained below. The last part shows the results obtained for different vessel inclinations and for two different series of parameters.

Simulations for a Blunt Profile

The simulation is performed in the following way:
1. The transducer used for the simulation is a linear array transducer with 64 elements of dimensions: 0.25 mm width, 5 mm height and a kerf or separation between elements of 0.05 mm. It gives the possibility of electronic focusing and apodization. A Hanning apodization is used for both emission and reception. The emit focus is set to be at an infinite distance from the transducer, so that a plane wave front is found at the measurement area. Short ultrasound pulses are simulated to be emitted every $T_{prf}$ seconds.
2. The generation of simulated data must include an artificial phantom consisting of point scatterers. This phantom simulates a blood vessel close to the skin surface at a depth of 30 mm. The angle between the blood vessel and the axial ultrasound beam is called 0, see FIG. 4. The phantom will be propagated a distance $\Delta r=vT_{prf}$ in the interval between two consecutive ultrasound pulse emissions to simulate the displacement of the scatterers. In the first simulations a blunt profile is considered, so that all scatterers move at the same velocity that was set to be 0.5 m/s.
3. For every ultrasound pulse, an individual simulation for each element of the transducer is done by the Field II program and stored. The field program is called 64 times for each of the transducer elements and for each pulse emission.
4. The focused beam is calculated as a transverse beam situated at a depth of 30 mm, in the middle of the region of interest. It uses the data obtained in the previous step. The line, transverse to the ultrasound beam has the same length as the transducer, i.e. 20 mm. The separation between two focus points was chosen to be dx=0.02 mm, which gives a total of 1000 samples for the transverse beam. The value of the field in each focus point is found by calculating the time that it takes the ultrasound wave to travel from each of the transducer elements to the field point and back to the transducer. This is $$\text{delay}=2/c\sqrt{(x_f-x_c)^2+(y_f-y_c)^2+(z_f-z_c)^2} \quad (22)$$

where $(x_c,c_y,z_c)$ are the positions of the center of the physical elements of the aperture and $(x_f,y_f,z_f)$ the position of each point in the transverse line. Three delay lines for the first, middle and last points of the transverse line have been plotted in FIG. 5 (continuous line).

The field value in each focus or transverse sampling point is the sum of the fields values obtained for each channel at the times that corresponds to the calculated delay line. The signal constructed this way is stored for each ultrasound emission.

At the same time and for each emission, a second signal is synthesized. It corresponds to the lateral beam where the axial movement of the scatterers has been compensated for. In this case the delays are $$\text{delay}' = \frac{2}{c}\sqrt{(x_f - x_c)^2 + (y_f - y_c)^2 + (z_f - z_c)^2} - \frac{2v_z}{c}T_{prf} \quad (23)$$

Figure 5:
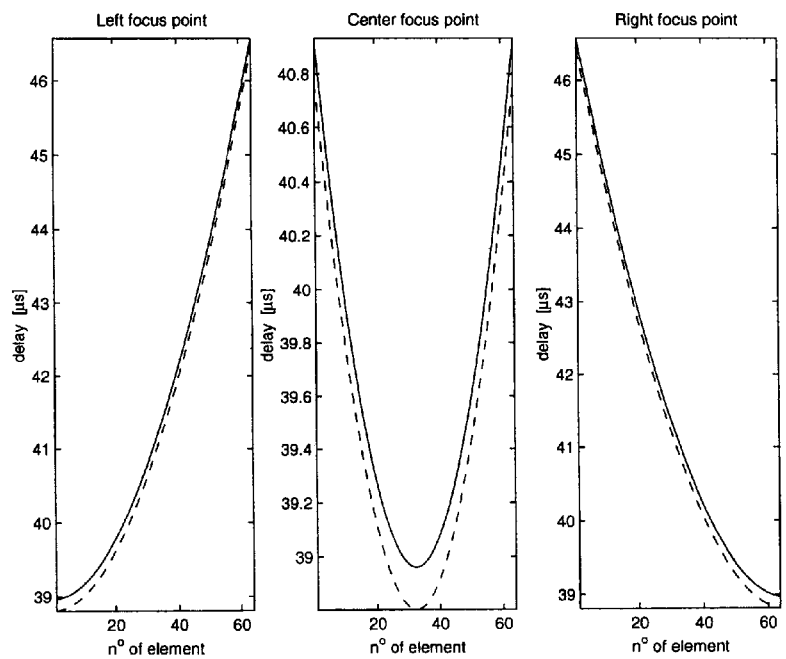
FIG. 5 shows delay graphs for the first, middle and last focus point of a transverse line og length 10 mm perpendicular to the z-axis. The dashed curves represent the delay lines compensated for the axial velocity of the scatterers when $\theta=30°$, $v=0.5$ m/s and $T_{prf}=1/3500$ s.
Figure 6:
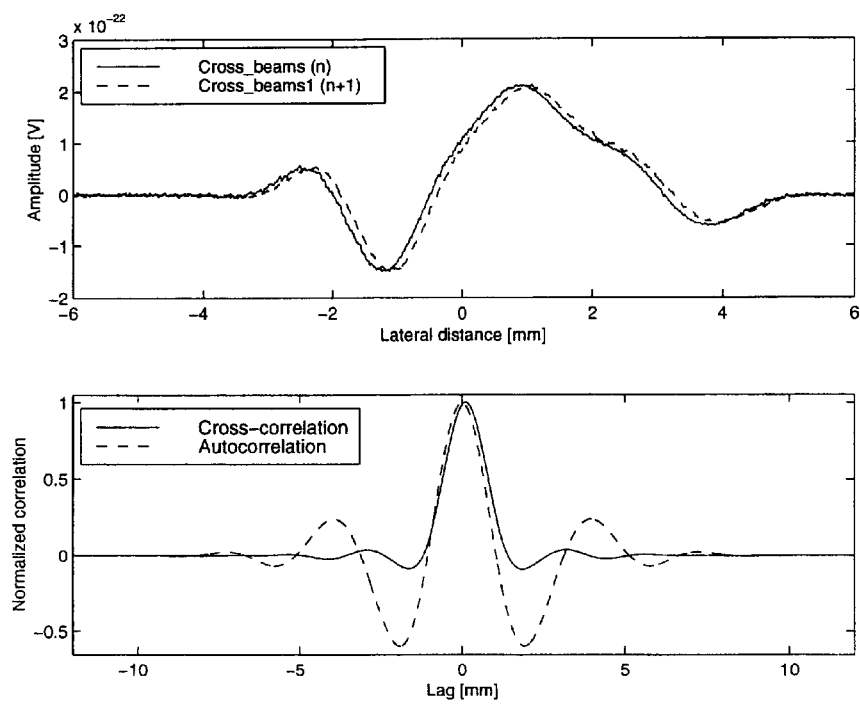
In FIG. 6 the top graph shows two consecutive lateral signals, where the second signal is compensated for the axial movement. The displacement, thus, corresponds to the transverse motion. In the bottom graph it has been evaluated by the cross-correlation method. Simulation was performed for θ=60°, v=0.5 m/s and dx=0.01 mm.

These new delay lines are plotted as dashed lines in FIG. 5. The axial velocity ($v_z$) needs to be estimated before the calculation of the compensated delay lines.

Estimation of the Velocity

The signals obtained from the simulation are used to estimate the velocity. The velocities are estimated by cross-correlating two consecutive signals in which the second signal is compensated for the axial motion that takes place during the pulse time interval. The position of the cross-correlation peak then indicates the shift of the signals.

The transverse velocity is found from $$\hat{v}_x = \frac{dl}{T_{prf}} \cdot n_{int}, \quad (24)$$

where $n_{int}$ is the interpolated index found by fitting a parabola around the maximum in the cross-correlation function [8].

Simulations and Results

Figure 9:
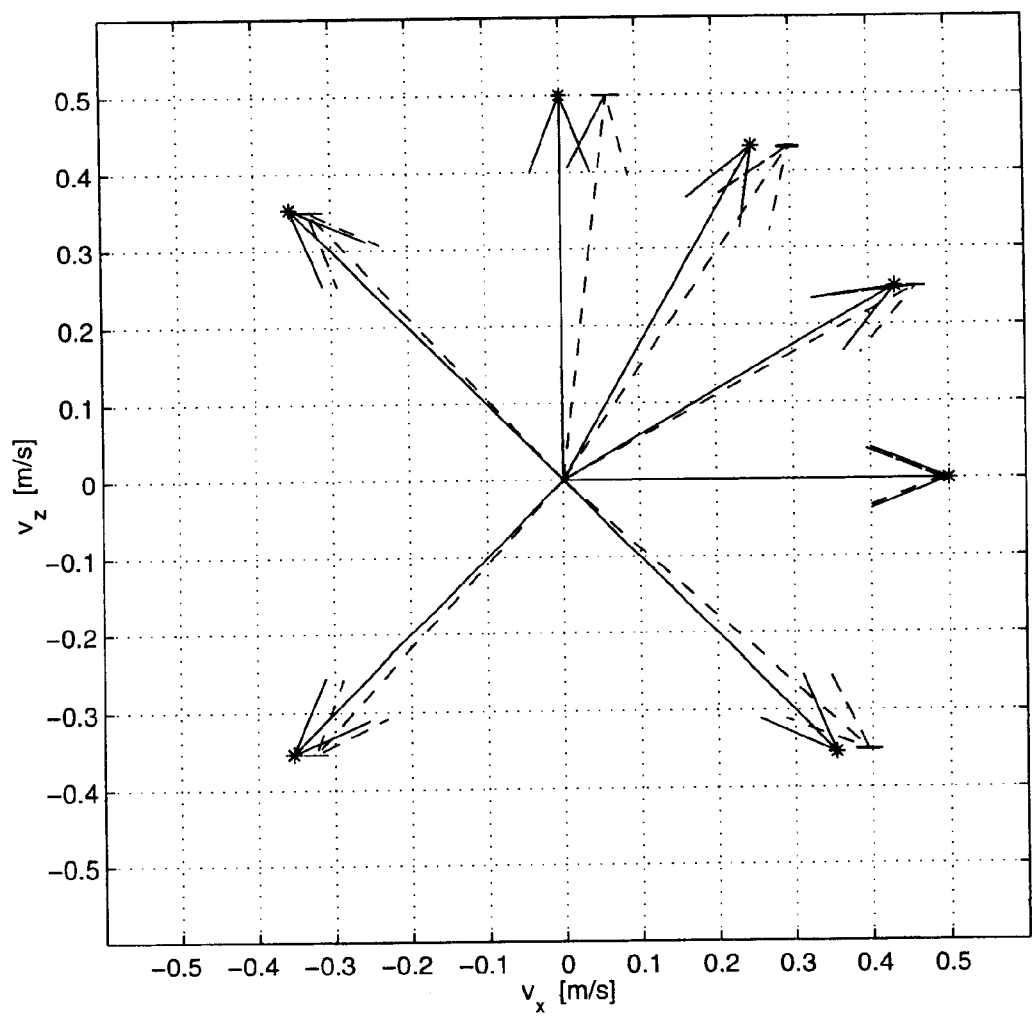
In FIG. 9 the continuous line arrows show the real velocity, and the dashed line arrows show the estimated velocity: $v_{est}=(\hat{v}_x,\hat{v}_z)$ for plug flow. The angle θ is measured clockwise from the vertical axis.
Figure 10:
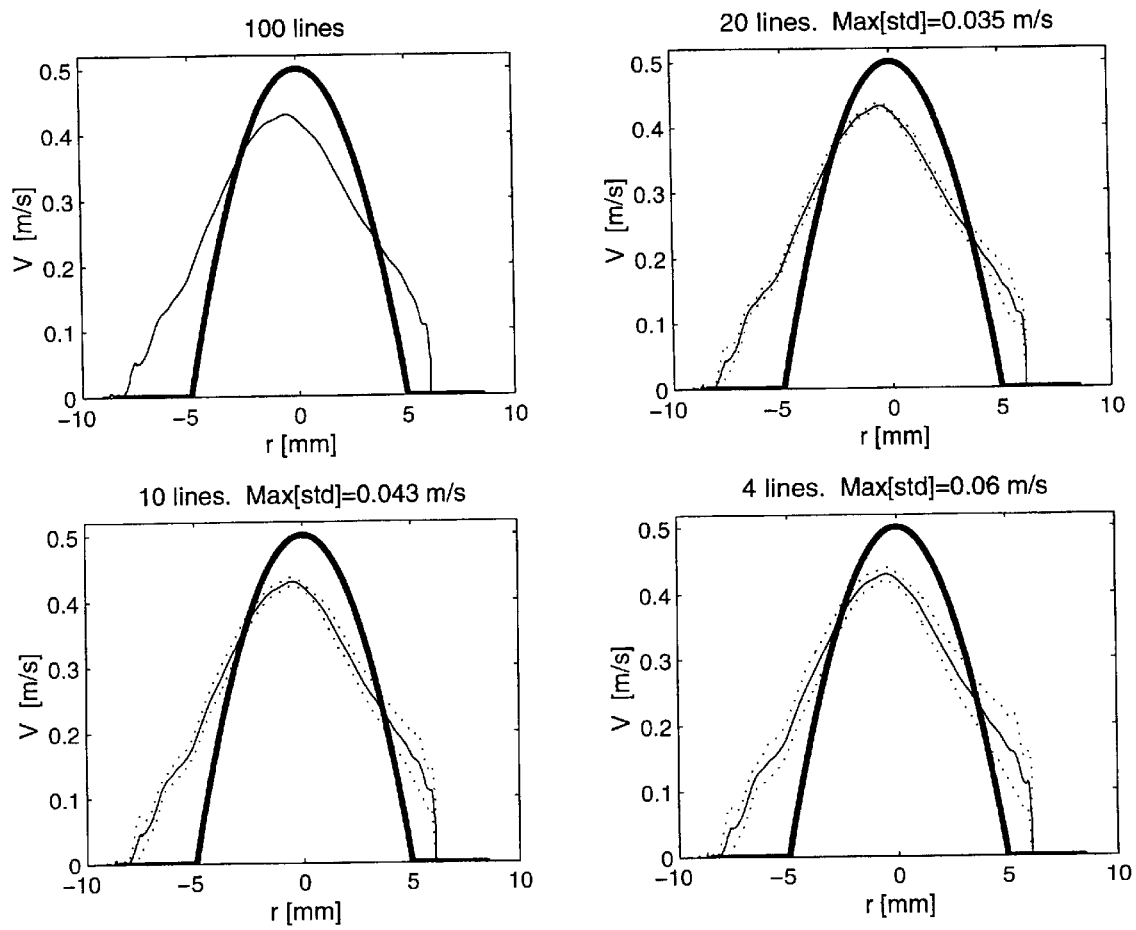
FIG. 10 shows estimated velocity profiles for θ=30° using 100, 20, 10 and 4 lines. The thick lines indicate the true velocity profile, the continuous line is the mean of the estimates, and the dotted lines are the standard deviations.
Figure 11:
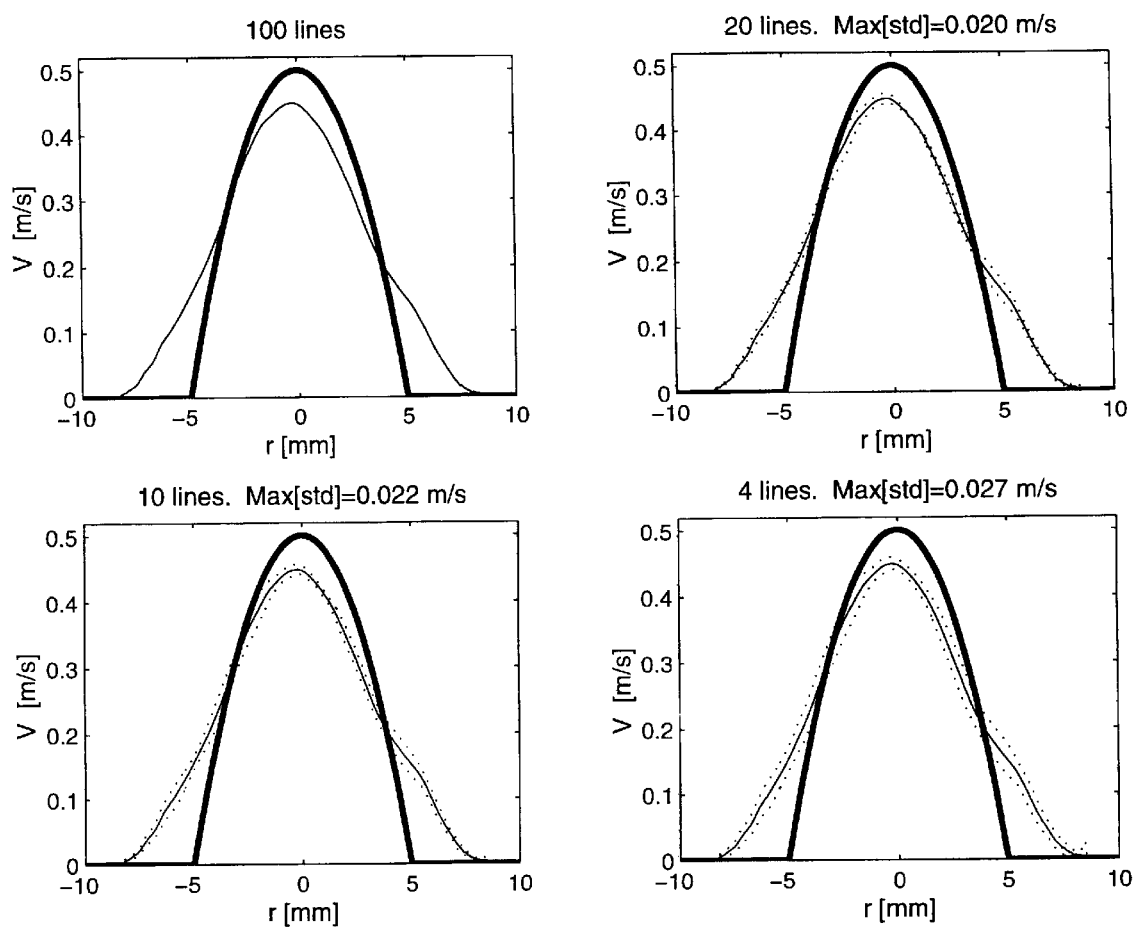
FIG. 11 shows estimated velocity profiles for θ=45° using 100, 20, 10 and 4 lines. The thick lines indicate the true velocity profile, the continuous line is the mean of the estimates, and the dotted lines are the standard deviations.
Figure 12:
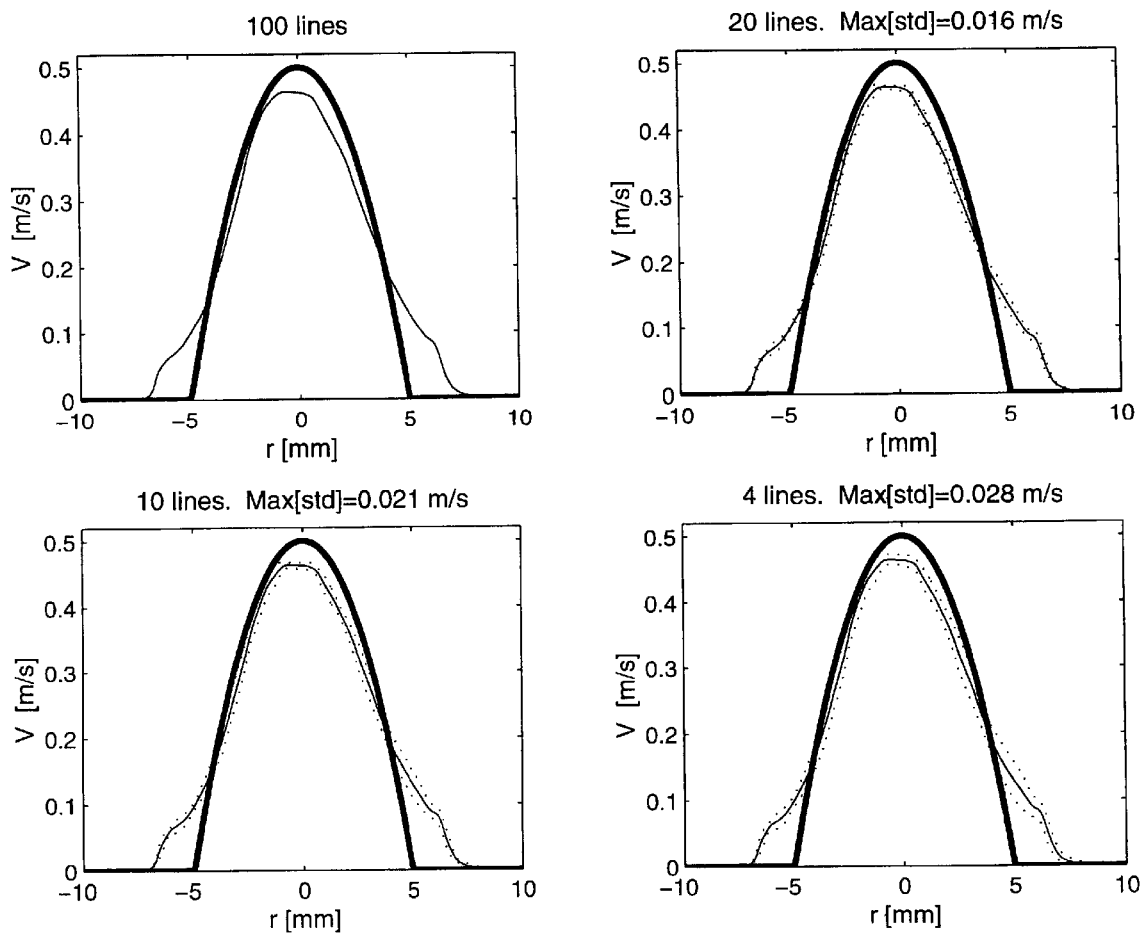
FIG. 12 shows estimated velocity profiles for θ=60° using 100, 20, 10 and 4 lines. The thick lines indicate the true velocity profile, the continuous line is the mean of the estimates, and the dotted lines are the standard deviations.
Figure 13:
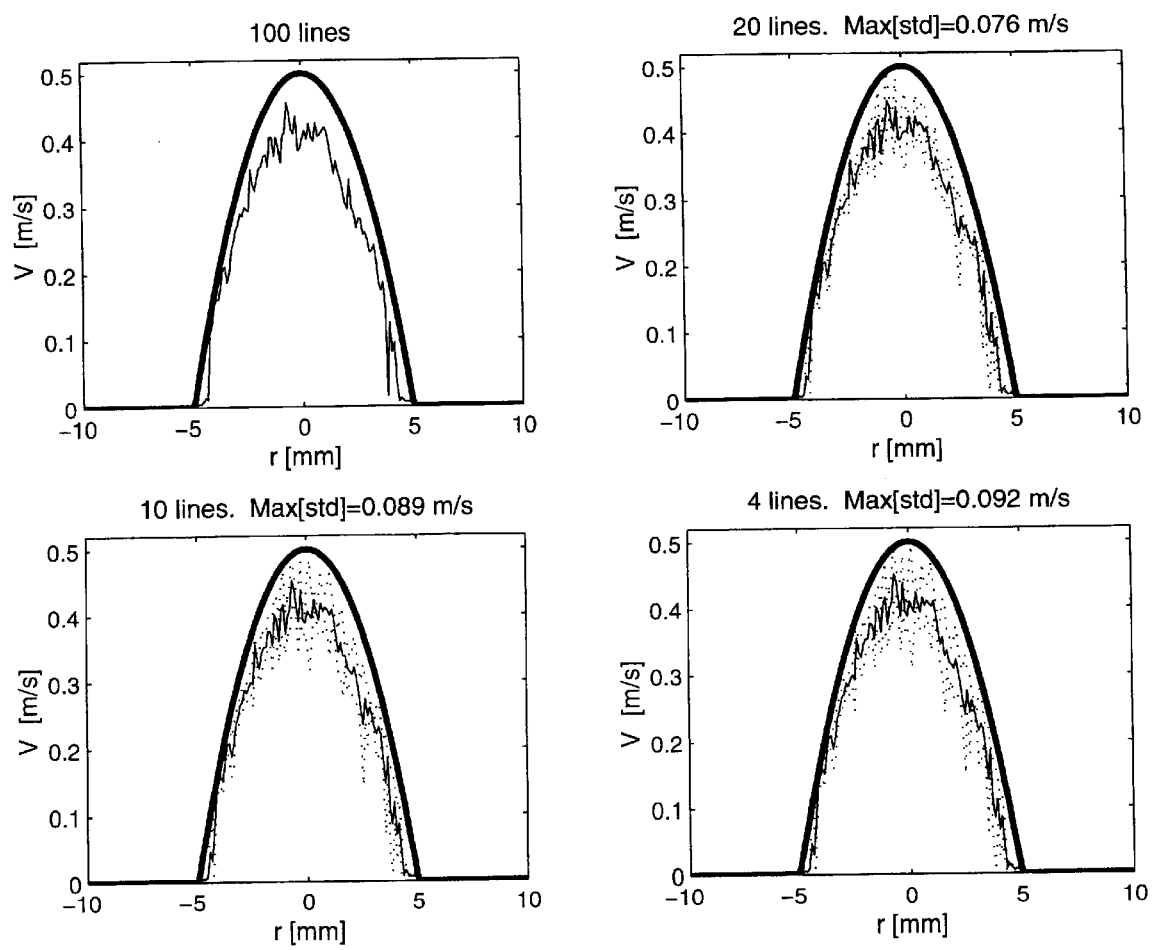
FIG. 13 shows estimated velocity profiles for θ=90° using 100, 20, 10 and 4 lines. The thick lines indicate the true velocity profile, the continuous line is the mean of the estimates, and the dotted lines are the standard deviations.

FIG. 9 shows the result of the simulations. They were performed for a blunt profile and for a scatterer velocity equal to v=0.5 m/s. The scatterer patterns were generated for seven different angles between the vessel and the axial beam. The received signals were found for 20 different pulse emissions. The cross-correlation estimator used 4 consecutive lines. This gave a total of 16 estimates for each velocity value. The dashed arrows point to (mean($\hat{v}_x$),mean($\hat{v}_z$)) for each angle, while the continuous line arrows represent the true values. The standard deviation is represented for each estimated point as the axis of the following ellipse:

$$\left(\frac{mean(\hat{v}_x)}{std(\hat{v}_x)}\right)^2 + \left(\frac{mean(\hat{v}_z)}{std(\hat{v}_z)}\right)^2 = 1 \quad (25)$$

The simulation parameters are shown in Table 1 and the results are plotted in FIG. 9 and listed in Table 2.

Estimation of the Velocity for a Parabolic Profile

The received signals are now focused along the flow direction. The lateral beams are tilted in order to follow the motion of the scatterers, see FIG. 3. The inclination of the vessel has to be known or estimated with a B-mode image for the calculation of the flow beams.

In the simulation a box of 20×10×20 mm³ is created. It contains 10 point-scatterers per cubic wavelength. The position and amplitude of the scatterers are randomly generated. The box of scatterers is rotated an angle $\phi=\pi/2-\theta$ to simulate the vessel inclination. The 'vessel' has a radius of 5 mm and is situated at a depth of 30 mm from the transducer. The scatterers that lie within the vessel wall are propagated between two consecutive pulses. The velocity profile is parabolic and the velocity in the center of the vessel is 0.5 m/s.

For each ultrasound pulse i, the data, with the positions and amplitudes of the scatterers, is loaded. Then, a scan for each of the channels of the array transducer is done. Finally, the delay lines for each focusing line are calculated and the flow beams are generated by adding the responses that correspond to the delay lines.

The transducer used was a linear array with 64 elements as described in Section 5.1. The parameters used for the simulation are listed in Table 3.

Figure 7:
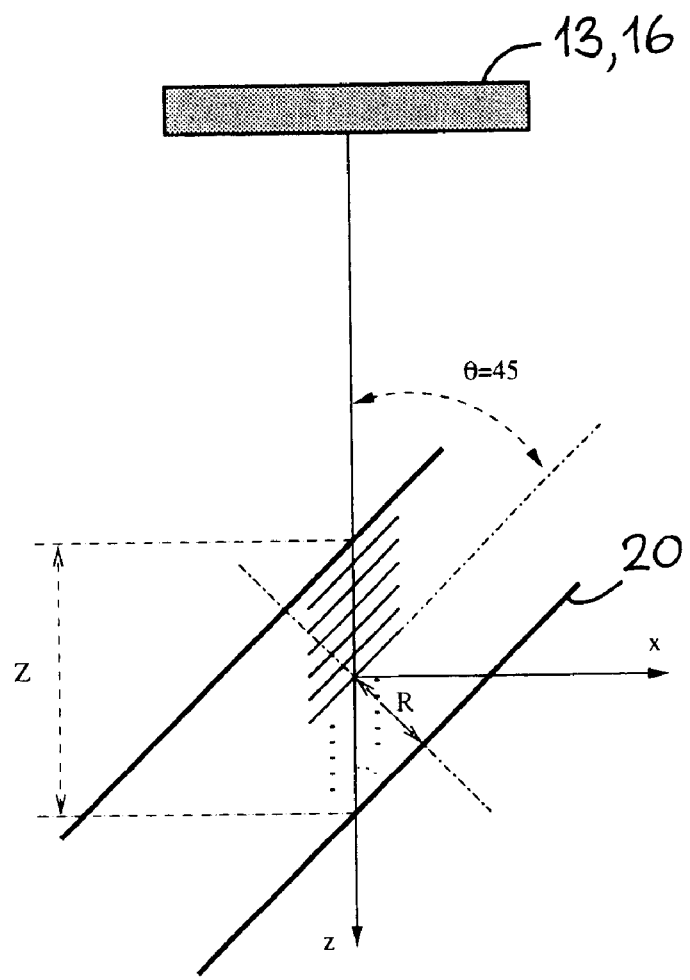
FIG. 7 shows the definition of depth in the vessel.

The focused lines had a length of 10 mm. They are rotated to have the same direction as the flow lines (see FIG. 7). They have to cover an axial distance of at least $$Z(\Theta) = \frac{2R}{\sin\Theta} \quad (26)$$

This length assures that there will be flow-beams in all the cross-section of the vessel. For small values of θ, the axial range-gate has to be increased. Z(θ) is divided in small segments, and for each of them a focusing line is calculated. The axial and lateral interval values used in the simulation are given in Table 4.

Figure 8:
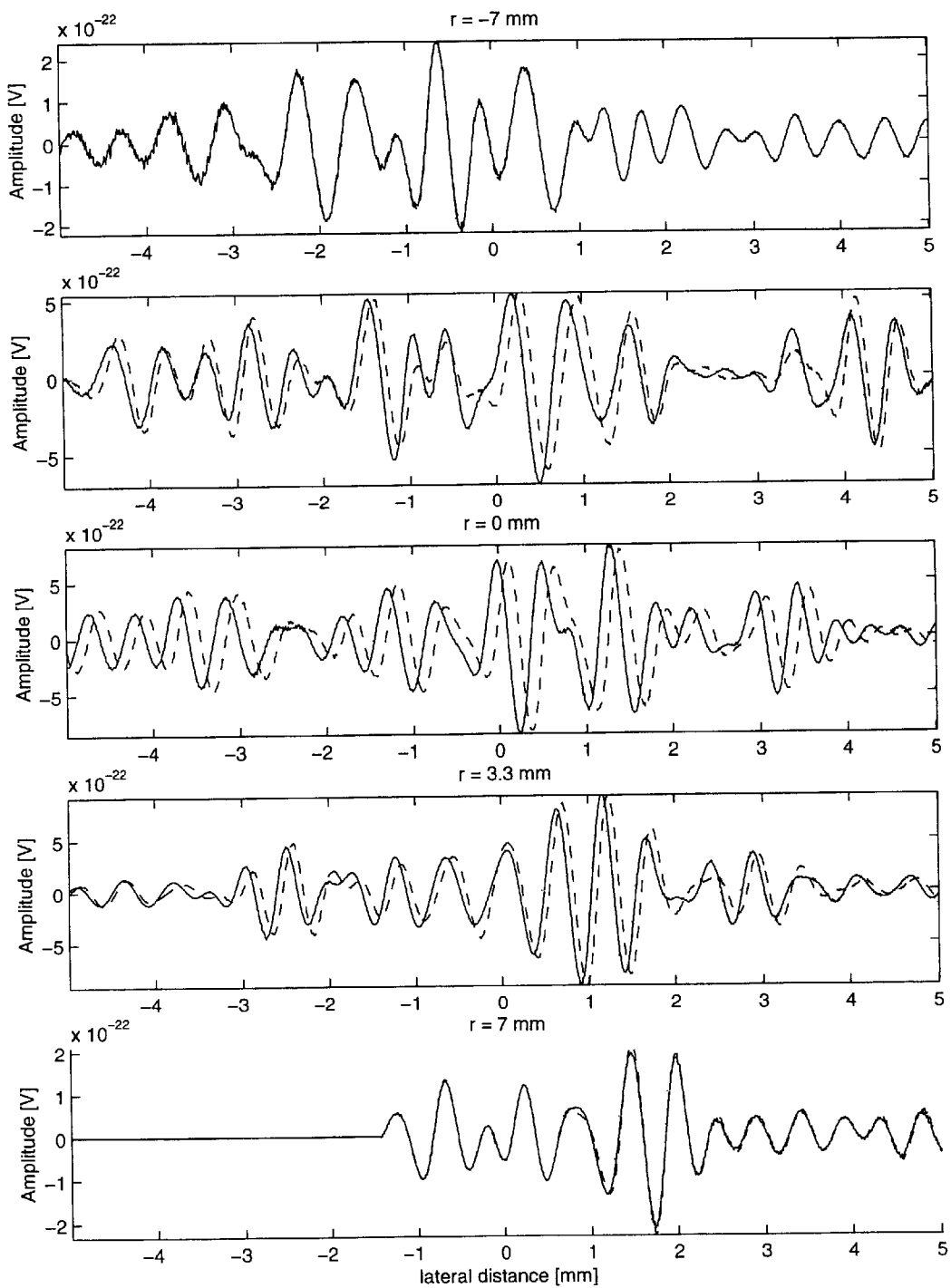
FIG. 8 shows the evolution of the lateral signals from two ultrasound pulses: pulse (i) is the continuous line, and pulse (I+1) is the dashed line. Five different points of the cross-section of the vessel are shown. The distance is measured from the center axis of the vessel. The data correspond to an inclination of the vessel of θ=60°, see also FIG. 12.

The velocity estimates are found from the simulated data. The velocity map is calculated by the cross-correlation of two received signals. These signals have been plotted in FIG. 8 for five different depths. The continuous lines represents the first signals and the dashed lines the second. The motion of the scatterers can be appreciated by the displacement of the signals. In the center of the vessel (r=0) the largest shift in position is observed. This shift decreases with the distance to the axis, and a parabolic profile can be recognized.

Once the cross-correlation function is calculated and averaged over a number of lines (4, 10, 20 or 100 for this simulation), the index of the maximum in the cross-correlation is obtained and interpolated, and the velocity is found from (24).

The minimum velocity that can be obtained is limited by the lateral sampling interval (dl), and the maximum value is determined by the lag in the cross-correlation function:

$$v_{min} = \frac{dl}{T_{prf}} \quad (27)$$

$$v_{max} = \frac{dl}{T_{prf}} \cdot lag \quad (28)$$

For the values introduced in the simulation: dl=0.01 mm, $T_{prf}$=1/3500 s and a sampling transverse line of 10 mm, this gives 10/0.01=1000 sampling points and the limits for the velocity estimation are $$v_{min}=0.035 \text{ m/s} \quad (29)$$

$$v_{max}=0.035 \cdot 1000=35 \text{ m/s} \quad (30)$$

The simulation was repeated for four inclinations of the vessel, θ=30, 45, 60, and 90°. For each angle, the estimates were found when averaging over 4, 10, 20 or 100 lines in the cross-correlation, which gave a total of 96, 90, 80 or 1 velocity estimates respectively for every lateral beam. The results are plotted in figures: 10, 11, 12, and 13. The thick line is the true velocity profile, the continuous line is the mean of the estimates, and the dotted lines are the standard deviations of the estimates.

The error in the velocity estimation is represented by the mean and the standard deviation of the vertical distance between the true and the estimated velocity profile (Table 5). The values in the table are when using 4 lines for calculating the cross-correlation.

TABLE 1

Parameters used for the blunt profile simulation. The emit focal distance is 150 mm.

| Center frequency $f_0$[Hz] | Wavelength $\lambda = c/f_0$ [m] | Number of cycles M | Sampling frequency $f_s$ [Hz] | Pulse repetition period $T_{prf}$ [s] | Number of scatterers N | Transversal interval dx [m] |
|---|---|---|---|---|---|---|
| 3 10⁶ | 0.51 10⁻³ | 2 | 100 10⁶ | 1/3500 | 5000 | 0.01 10⁻³ |

TABLE 2

| Θ[deg] | 0 | 30 | 60 | 90 | 135 | −135 | −45 |
|---|---|---|---|---|---|---|---|
| True $v_x$ [m/s] | 0 | 0.25 | 0.43 | 0.5 | 0.35 | −0.35 | −0.35 |
| Mean $[\hat{v}]_x$ [m/s] | 0.067 | 0.245 | 0.407 | 0.449 | 0.342 | −0.303 | −0.309 |
| Std $[\hat{v}]_x$ [m/s] | 0.008 | 0.033 | 0.014 | 0.019 | 0.018 | 0.023 | 0.016 |
| Error [%] | — | −2 | −5.3 | −10.2 | 2.2 | 13.4 | 11.7 |
| Accuracy [%] | 11.9 | 13.4 | 3.4 | 4.2 | 5.2 | 7.5 | 5.1 |

Values of the real transverse velocity and the estimates mean and standard deviation for 5000 scatterers and an emit focal distance of 150 mm. The error is calculated as: (mean($\hat{v}_x$) − $v_x$)/$v_x$, and the accuracy is mean($\hat{v}_x$ − $v_x$)/std($\hat{v}_x$).

TABLE 3

Parameters used for the parabolic profile simulation.

| Center frequency $f_0$ [Hz] | Wavelength $\lambda = c/f_0$ [m] | Number of Sampling cycles M | Sampling frequency $f_s$ [Hz] | Pulse repetition period $T_{prf}$ [s] | Focal distance F [m] |
|---|---|---|---|---|---|
| $3 \cdot 10^6$ | $0.51 \cdot 10^{-3}$ | 2 | $100 \cdot 10^6$ | 1/3500 | 150 |

TABLE 4

Values of the lateral and axial intervals used in the simulations.

| Lateral line length [m] | Lateral interval [m] | Axial length [m] | Axial interval [m] |
|---|---|---|---|
| $10 \cdot 10^{-3}$ | $0.01 \cdot 10^{-3}$ | Z(θ) | $0.1 \cdot 10^{-3}$ |

TABLE 5

Mean and standard deviation of the distance between the true profile and the estimated one. They are calculated for a different cross-section distance for each of the angles so that only the significant part of the plots are taken into account: $r \in [-8.5, 6]$ for θ = 30°, $r \in [-8.3, 8.3]$ for θ = 45°, $r \in [-8, 8]$ for θ = 60°, $r \in [-5, 5]$ for θ = 90° (r indicates distance to the center of the vessel in [mm]).

| θ [deg] | 30 | 45 | 60 | 90 |
|---|---|---|---|---|
| Mean $|\hat{v} - v|$ [m/s] | 0.081 | 0.056 | 0.04 | 0.073 |
| Std $|\hat{v} - v|$ [m/s] | 0.047 | 0.038 | 0.029 | 0.029 |

References

[1] D. J. Phillips, K. W. Beach, and J. Primozich D. E. Strandness. Should results of ultrasound Doppler studies be reported in units of frequency or velocity? *Ultrasound Med. Biol.*, 15:205–212, 1989.

[2] U. Moser. Verfahren und Messanordnung zum Messen des Volumenstromes in einer Schicht mit reflektierender Struktur, European patent application, publication number 616 231 A2.

[3] M. D. Fox. Multiple crossed-beam ultrasound Doppler velocimetry. IEEE *Trans. Son. Ultrason.*, SU-25:281–286, 1978.

[4] G. E. Trahey, J. W. Allison, and O. T. von Ramm. Angle independent ultrasonic detection of blood flow. *IEEE Trans. Biomed. Eng.*, BME-34:965–967, 1987.

[5] V. L. Newhouse, D. Censor, T. Vontz, J. A. Cisneros, and B. B. Goldberg. Ultrasound Doppler probing of flows transverse with respect to beam axis. *IEEE Trans. Biomed. Eng.*, BME-34:779–788, 1987.

[6] O. Bonnefous. Measurement of the complete (3D) velocity vector of blood flows. In *Proc. IEEE Ultrason. Symp.*, pages 795–799, 1988.

[7] J. A. Jensen and N. B. Svendsen. Calculation of pressure fields from arbitrarily shaped, apodized, and excited ultrasound transducers. IEEE Trans. Ultrason., *Ferroelec., Freq. Contr.*, 39:262–267, 1992.

[8] J. A. Jensen. Estimation of *Blood Velocities Using Ultrasound: A Signal Processing Approach*. Cambridge University Press, New York, 1996.

What is claimed is:

1. An apparatus for measuring the velocity of a moving object or a collection of moving objects moving in a predetermined direction and at a predetermined distance, the apparatus comprising:

a generator for generating excitation signals, an emitting transducer for transforming the excitation signals into wave energy and for emitting said wave energy in a predetermined direction of propagation towards the object or objects, a receiving transducer for receiving from said moving object or objects, signals generated by interaction with said wave energy emitted from said emitting transducer, said emitting transducer and said receiving transducer having respective sensitivities for selectively creating a plurality of focal points, which in combination define a focus line at the predetermined distance and extending in the predetermined direction of movement, and means for calculating a correction of signals received from the moving object or objects on the focus line, and for calculating, based on the correlation, the velocity of the moving object or objects in the direction of the focus line.

2. An apparatus according to claim 1 wherein said wave energy is pulsed wave.

3. An apparatus according to claim 1 wherein said wave energy is sound energy.

4. An apparatus according to claim 1 wherein said sound energy is ultrasound energy.

5. An apparatus according to claim 1 wherein said wave energy is electromagnetic energy.

6. An apparatus according to claim 1 wherein said emitting transducer is an array transducer including a plurality of emitting transducer elements.

7. An apparatus according to claim 6 further comprising an emit beam former for receiving said generating excitation signals and for supplying each of said plurality of emitting transducer elements with individual excitation signals each having a predetermined time delay relative to the others of said individual excitation signals.

8. An apparatus according to claim 7 wherein said individual excitation signals have time delays resulting in focused wave energy being emitted.

9. An apparatus according to claim 1 wherein said receiving transducer is an array transducer including a plurality of receiving transducer elements.

10. An apparatus according to claim 9 further comprising a receive beam former for receiving signals from said plurality of receiving transducer elements and for delaying each of said signals from said plurality of receiving transducer elements individually relative to the others of said signals from said plurality of receiving transducer elements.

11. A method for measuring the velocity of a moving object or a collection of moving objects moving in a predetermined direction and at a predetermined distance, the method comprising:

emitting excitation signals of pulses of wave energy in a predetermined direction of propagation towards the object or objects, receiving from said moving object or objects, reflected signals resulting from interaction of emitted wave energy with the moving object or objects, the emission of excitation signals and the reception of reflected signals having respective sensitivities for selectively creating a plurality of focal points, which in combination define a focus line at the predetermined distance and extending in the predetermined direction, calculating a correlation of signals received from the moving object or objects on the focus line, and calculating, based on the correlation, the velocity of the moving object or objects in the direction of the focus line.

12. A method according to claim 11 wherein said wave energy is pulsed wave energy.

13. A method according to claim 11 wherein said wave energy is sound energy.

14. A method according to claim 11 wherein said sound energy is ultrasound energy.

15. A method according to claim 11 wherein said wave energy is electromagnetic energy.

16. A method according to claim 11 wherein said emitting transducer is an array transducer including a plurality of emitting transducer elements.

17. An method according to claim 16 further comprising an emit beam former for receiving said generating excitation signals and for supplying each of said plurality of emitting transducer elements with individual excitation signals each having a predetermined time delay relative to the others of said individual excitation signals.

18. A method according to claim 17 wherein said individual excitation signals have time delays resulting in focused wave energy being emitted.

19. A method according to claim 11 wherein said receiving transducer is an array transducer including a plurality of receiving transducer elements.

20. A method according to claim 19 further comprising a receive beam former for receiving signals from said plurality of receiving transducer elements and for delaying each of said signals from said plurality of receiving transducer elements individually relative to the others of said signals from said plurality of receiving transducer elements.

* * * * *